United States Patent [19]

Swailes et al.

[11] 4,107,293
[45] Aug. 15, 1978

[54] ATTRACTANT FOR DARKSIDED CUTWORM MOTH

[75] Inventors: G. Edward Swailes; Dean L. Struble, both of Lethbridge, Canada

[73] Assignee: Canadian Patents and Development Limited, Ottawa, Canada

[21] Appl. No.: 781,507

[22] Filed: Mar. 25, 1977

[51] Int. Cl.$^2$ ............................................. A01N 17/14
[52] U.S. Cl. ....................................................... 424/84
[58] Field of Search .......................................... 424/84

[56] References Cited

U.S. PATENT DOCUMENTS

| 3,586,712 | 6/1971 | Green et al. | 424/84 |
| 3,702,358 | 11/1972 | Green et al. | 424/84 |
| 3,996,270 | 12/1976 | Friedman et al. | 424/84 |

OTHER PUBLICATIONS

Chemical Abstracts vol. 82: 39470w (1975); vol. 83: 202687d (1975); vol. 84: 16718k, 148048b, 176957r & p. 2439cs (1976).

J. of Economic Entomology vol. 67, No. 2, pp. 211–216 and vol. 68, No. 4, pp. 423–427 (1975).

Science vol. 181, pp. 661–663 (1973).

*Primary Examiner*—Donald B. Moyer
*Attorney, Agent, or Firm*—Alan A. Thomson

[57] ABSTRACT

An attractant for male moths of the darksided cutworm *Euxoa messoria* (Harris) comprises
(1) Z-11-hexadecen-1-yl acetate, and
(2) Z-7 compound selected from Z-7-hexadecen-1-yl acetate and Z-7, Z-11-hexadecadien-1-yl acetate in ratios (1)/(2) within about 4:1 to 40:1. The mixture may also include the E isomers, E-11-hexadecen-1-yl acetate and E-7-hexadecen-1-yl acetate, in amounts up to about 20% of the total mixture.

7 Claims, No Drawings

ATTRACTANT FOR DARKSIDED CUTWORM MOTH

FIELD OF THE INVENTION

This invention is concerned with sex pheromone attractants for male moths of the darksided cutworm *Euxoa messoria* (Harris). A very effective and specific attractant mixture has been found which would be useful in monitoring and helping to control this species.

DESCRIPTION OF THE PRIOR ART

Attractants for male moths of some armyworms and cutworms have recently been found. The components of the attractants are usually based on alkenols (or aldehydes or esters thereof) having from about 8 to 16 carbon atoms. The position and stereoisomer of the double bond in each component is critical for each species. It has not been possible to predict attractant components and their proportions for a given species from a knowledge of attractants for other similar species. Laboratory stimulation tests such as electroantennograms do not correlate well with field attractancy and extensive trial-and-error testing under field conditions is required.

No references to attractants for the darksided cutworm have been noted. This cutworm has been recorded throughout North America and the larvae feed on numerous crops. The habits, distribution and economic importance of this cutworm are described in Research Circular 205, An Annotated Bibliography of the Darksided Cutworm, *Euxoa messoria* (Harris) (R. W. Rings, B. A. Johnson, and F. J. Arnold. December, 1975. Ohio Agricultural Research and Development Center, Wooster, Ohio).

SUMMARY OF THE INVENTION

By extensive field testing of a large number of synthetic compounds and mixtures, an attractant composition has been found for the darksided cutworm *Euxoa messoria* (Harris) comprising (1) Z-11-hexadecen-1-yl acetate, and
(2) Z-7 compound selected from Z-7-hexadecen-1-yl acetate and Z-7, Z-11-hexadecadien-1-yl acetate and mixtures thereof, in ratios of (1)/(2) within about 4:1 to about 40:1.

Preferably component (2) is Z-7-hexadecen-1-yl acetate, and the proportion of (1) to (2) is approximately 20:1. Up to about 20% of the mixture may be comprised of the E isomers, E-11-hexadecen-1-yl acetate and E-7-hexadecen-1-yl acetate, without significant interference with the attractant effectiveness.

Any suitable inert solid or liquid carrier can be used for this attractant as will be evident to those skilled in this art. We have found a solid rubber carrier to be very suitable. The attractant may be applied to this carrier by various methods such as applying an n-hexane solution of the attractant to the rubber. The most suitable amount of attractant per trap has been found to be from about 100 to about 1000 micrograms.

DETAILED DESCRIPTION AND TEST RESULTS

Field screening was done in early tests with 105 olefinic compounds of the decen-1-yl to hexadecen-1-yl series. Of these acetates and alcohols, 89 were synthesized by reactions similar to those previously described in the literature and seven monoolefinic and nine diolefinic acetates were obtained from commercial sources.

The monoolefinic acetates were purified by argentation liquid chromatography using Amberlyst® XN-1005 resin (trademark Rohm and Haas) impregnated with silver nitrate (Emken, E. A., C. R. Scholfield, and H. J. Dutton. 1964. Chromatographic separation of cis- and trans-fatty esters by argentation with a macroreticular exchange resin. *J. Am. Oil Chem. Soc.* 41: 388-390). The isomerically pure acetates were hydrolyzed to the corresponding alcohols in the usual manner. The acetates and alcohols were further purified by preparative gas liquid chromatography (pglc). The purified acetates contained no detectable geometric isomers by glc. The acetates contained no detectable positional isomers ($<1.0\%$) by ozonolysis. The Z7,Z11-16:Ac was purified by argentation chromatography followed by pglc and it contained no detectable geometric isomers ($<0.05\%$) or Z7-16:Ac ($<0.01\%$).

In later tests, the Z7-16:Ac and Z11-16:Ac were purchased commercially and were purified in a similar manner except that Lewatit® SP-1080 GR resin (trademark E. Merck) was used in the argentation chromatrography (Houx, N. W. H., S. Voerman, and W. M. F. Jongen. 1974. Purification and analysis of synthetic insect sex attractants by liquid chromatography on a silver-loaded resin. *J. Chrom.* 96: 25-32). At least 300 combinations of compounds were tested in various weight ratios.

The attractants carriers were rubber bands and, unless otherwise stated, the test compounds were at 200 $\mu$g/carrier. In early tests, the carriers were placed inside shields of polyethylene screen, but these were omitted in the latter tests.

The traps for field testing were placed between strips of fallow and wheat at two sites in Alberta, and one in Manitoba. In later tests, some of the traps were made of galvanized metal with metal screen end-cones with an apical hole 1.0 cm in diameter. The traps were set on wooden stakes 10 to 45 m apart, at a height of 1 m, and in a single row from north to south. One end of the traps faced the prevailing, west, wind. In all replicated tests, the treatments were randomized in four blocks within a single row of traps and one attractant trap was used at each end of the row beyond the replicated treatments. The moth catches were recorded and the traps emptied every second or third day, and the data were analyzed by Tukey's multiple range test (Steel, R. G. D. and J. H. Torrie. 1960. Principles and procedures of statistics. McGraw-Hill Book Co., New York. 481 pp.). The later data were transformed to $\log(X+1)$ for the analysis of variance and the geometrical mean daily catches are reported.

Female darksided cutworm moths were used to bait some of the traps as controls. The female moths were stored at 10° C with a food supply for a minimum of 5 days before they were used in the field tests.

Summaries of typical test results are given in Tables I to VI.

Table I.

| Combinations of Compounds | Ratios | Males captured 26 Aug.-10 Sept. | 11 Sept.-6 Oct. |
|---|---|---|---|
| Compounds plus Z11-16:Ac | | | |
| Z7-16:Ac | 1:10 | 8 | 15 |
|  | 1:4 | 17 | 7 |
|  | 1:1 | 3 | — |
|  | 4:1 | 0 | 0 |
| E7-16:Ac | 1:4 | 0 | — |

Catches of male darksided cutworm moths in non-replicated treatments in Southern Alberta in 1975

Table I.-continued
Catches of male darksided cutworm moths in non-replicated treatments in Southern Alberta in 1975

| Combinations of Compounds | Ratios | Males captured 26 Aug.- 10 Sept. | 11 Sept.- 6 Oct. |
|---|---|---|---|
|  | 4:1 | 1 | — |
| Z7-15:Ac | 1:4 | 4 | 7 |
|  | 1:1 | 0 | 0 |
| Z7-14:Ac | 1:1 | — | 3 |
| Z7-13:Ac | 1:10 | 7 | — |
|  | 1:4 | 0 | 0 |
| Z7-16:Ac and Z11-16:Ac plus |  |  |  |
| E11-16:Ac | 1:4:1 | — | 10 |
|  | 1:8:1 | — | 41 |
|  | 2:8:1 | — | 14 |
|  | 2:16:1 | — | 23 |
| Z7-3 | 2:8:1 | — | 8 |
| Z11-16:OH* | 2:8:1 | 5 | — |
| E7-16:Ac | 1:10:1 | 4 | — |
|  | 3:10:1 | 3 | — |
| Z7-14:Ac | 1:4:1 | 3 | — |
| E11-16:Ac, 16:Ac | 2:20:1:4 | — | 15 |
| E11-16:Ac, E7-16:Ac | 2:20:1:1 | 17 | 15 |
| Z11-16:OH, Z7-16:OH † | 1:5:1:1 | — | 14 |

\* and † Male clover cutworm moths were also attracted: *, 32; ¹, 73

The darksided cutworm male moths were attracted to combinations of Z-7-hexadecen-1-yl acetate (Z7-16:Ac) and Z-11-hexadecen-1-yl acetate (Z11-16:Ac), and to combinations of these with E11-16:Ac (Table I). Darksided cutworm males were not attracted to any of the compounds when they were tested singly. Two dienes, Z7,Z11-16:Ac and Z7,E11-16:Ac, were also non-attractive. A few moths were attracted to combinations of Z11-16:Ac with each of Z7-15:Ac, Z7-14:Ac and Z7-13:Ac, even though these compounds differed from Z7-16:Ac by one to three methylene groups. Combinations of Z7-16:Ac and Z11-16:Ac with other selected compounds as third or fourth components did not reveal any outstanding improvement in the attractant. Male moths of the clover cutworm, *Scotogramma trifolii* (Rottenberg), were attracted to all of the combinations that contained Z11-16:Ac and Z11-16:OH, which was to be expected as this combination is a known attractant for clover cutworm (Struble, D. L. and G. E. Swailes. 1975. A sex attractant for the clover cutworm, *Scotogramma trifolii* (Rottenberg), a mixture of Z-11-hexadecen-1-ol acetate and Z-11-hexadecen-1-ol. *Environ. Ent.* 4: 632–636; Underhill, E. W., W. F. Steck, and M. D. Chisholm. 1976. Sex pheromone of the clover cutworm moth, *Scotogramma trifolii*: Isolation, identification and field studies. *Environ. Ent.* 5: 307–310). There was no advantage in using Z11-16:OH in the attractant for the darksided cutworm.

Some of the promising combinations from the nonreplicated treatments were tested in four replications. In early tests, the numbers of males attracted did not differ (P > 0.05) among the chemical combinations nor did they differ (P > 0.05) from the numbers attracted by the unmated females (Table II).

Table II
Mean daily catches of male darksided cutworm moths in four replications in southern Alberta in 1975

| Z7-16:Ac/Z11-16:Ac plus | Ratios | x̄ Males/trap/day ǂ from 8 Sept.- 8 Oct. | 11 Sept.- 6 Oct. | Total males captured |
|---|---|---|---|---|
| — | 1:10 | — | 0.53 | 53 |
| E11-16:Ac | 1:8:1 | 0.70 | — | 77 |
|  | 3:8:1 | 0.20 | — | 22 |
|  | 2:10:1 | — | 0.36 | 36 |
|  | 2:16:1 | 0.63 | — | 70 |
|  | 2:20:1 | — | 0.54 | 54 |
|  | 2:40:1 | — | 0.67 | 67 |

Table II-continued
Mean daily catches of male darksided cutworm moths in four replications in southern Alberta in 1975

| Z7-16:Ac/Z11-16:Ac plus | Ratios | x̄ Males/trap/day ǂ from 8 Sept.- 8 Oct. | 11 Sept.- 6 Oct. | Total males captured |
|---|---|---|---|---|
| Two unmated females/trap |  | 0.95 | — | 106 |
|  |  | — | 0.80 | 80 |
| Standard error/day |  | 0.163 | 0.155 | — |

ǂ The means within each test period were not different (P > 0.05).

Various ratios of Z7-16:Ac and Z11-16:Ac were tested in later tests and although the numbers of males attracted did not differ significantly (P > 0.05) among tests of the ratios of 1:10, 1:20, and 1:40, the greatest numbers of males per test period were attracted to the ratios of 1:20 and 1:40 (Table III). These two compounds plus E11-16:Ac were also tested in various ratios, but the numbers of males attracted to the combinations of the two and three components at similar ratios did not differ (P > 0.05, Tables III and IV). The presence of E11-16:Ac as tested did not significantly alter the catches of the males, thus it should not be necessary to remove the small amounts (2 to 9%) of the E-isomer that are usually produced during the synthesis of the Z11-16:Ac.

Five other compounds, Z7-16:OH, E7-16:Ac, E11-16:OH, 16:OH, and 16:Ac, were tested as additional components in the two- and three-component attractant. These additional components did not alter the catches of the males (P > 0.05, Tables III and IV).

Table III
Mean daily catches of male darksided cutworm moths in four replications in Alberta in 1976

| Z7-16:Ac/Z11-16:Ac plus | Ratios | x̄ Males/trap/day for 9 Aug.- 1 Sept. | 18 Aug.- 8 Sept.* | 3–20 Sept. |
|---|---|---|---|---|
| — | 1:3 | — | 0.47$^c$ | — |
| — | 1:10 | 0.51$^{ab}$ | 0.80$^{abc}$ | — |
| — | 1:10† | 0.18$^c$ | — | — |
| — | 1:20 | — | 1.10$^{ab}$ | 0.52$^a$ |
| — | 1:40 | — | — | 0.55$^a$ |
| E11-16:Ac | 1:10:1 | 0.63$^a$ | 1.10$^{ab}$ | — |
|  | 1:10:1† | 0.26$^{bc}$ | — | — |
|  | 2:40:1 | — | 1.3$^a$ | 0.41$^a$ |
|  | 1:16:3 | — | 1.23$^a$ | — |
|  | 3:16:3 | — | 0.94$^{abc}$ | — |
|  | 3:16:1 | — | 0.61$^{bc}$ | — |
| E11-16:Ac, E11-16:OH | 1:10:1:1 | — | 0.95$^{ab}$ | — |
|  | 1:10:1:3 | — | 1.20$^{ab}$ | — |
| E11-16:Ac, 16:OH | 2:40:1:5 | — | — | 0.64$^a$ |
| E11-16:Ac, 16:Ac | 2:40:1:5 | — | — | 0.29$^a$ |
| Z7,Z11-16:Ac ǂ | 1:9 | 0.46$^{ab}$ | — | — |
| Z7, Z11-16:Ac ǂ, E11-16:Ac | 1:9:1 | — | 1.01$^{ab}$ | — |
| Total males captured |  | 179 | 898 | 208 |

*Metal traps were used for this column, and the treatments were rerandomized once. Plastic traps were used for the other two columns. All traps were about 27 m apart. Means followed by the same letter do not differ (P > 0.05).
†These treatments were at 1 mg/carrier.
ǂ Z7,Z11-16:Ac was used in place of Z7-16:Ac.

Table IV
Mean daily catches of male darksided cutworm moths in four replications from 10–21 September 1976

| Compounds | Ratio | x̄ males/trap/day* |
|---|---|---|
| Z7-16:Ac, Z11-16:Ac plus |  |  |
| — | 1:40 | 0.52 |
| Z7-16:OH | 1:40:1 | 0.46 |
| E7-16:Ac | 1:40:1 | 0.78 |
| E11-16:OH | 1:40:5 | 0.57 |

Table IV-continued

Mean daily catches of male darksided cutworm
moths in four replications from 10–21 September 1976

| Compounds | Ratio | x̄ males/trap/day* |
|---|---|---|
| 16:OH | 1:40:5 | 0.61 |
| Z7-16:Ac, Z11-16:Ac, E11-16:Ac plus | | |
| — | 2:40:1 | 0.43 |
| — | 1:40:1 | 0.46 |
| Z7-16:OH | 1:40:1:1 | 0.39 |
| E7-16:Ac | 1:40:1:1 | 0.50 |
| E11-16:OH | 1:40:1:5 | 0.53 |
| 16:OH | 1:40:1:5 | 0.59 |
| Total males captured | | 338 |

*Metal traps were placed 45 m apart in a field in Alberta. The means do not differ (P > 0.05).

Although the males were attracted to combinations of Z7-16:Ac, and Z11-16:Ac, the diene Z7,Z11-16:Ac alone was non-attractive. The males were attracted, however, to a combination of Z7,Z11-16:Ac, and Z11-16:Ac in a ratio of about 1:9 but the numbers captured did not differ (P > 0.05) from those attracted to the two monoolefins at a ratio of 1:10 (Table III). The diene could be used in place of or along with Z7-16:Ac in the attractant, but it is not a necessary component.

A combination of Z7-16:Ac and Z11-16:Ac at a ratio of 1:10 and these compounds with E11-16:Ac at a ratio of 1:10:1 were tested at 200 μg and 1 mg/carrier. The greatest number of males (P > 0.05) were attracted to the 200 μg/carrier (Table III), so there was no advantage in using the attractant at 1 mg/carrier in the type of trap used in these tests.

The treatments in all of the replicated tests were substantially specific for the darksided cutworm males - out of about 2,000 moths captured, only 47 were of other species, mainly *Crymodes longula* Grote and *Helotropha reniformis* Grote.

The population of darksided cutworm adults was sparse throughout Alberta during the test periods, as they were not identified among any of the moths captured in 16 black light traps that were operated by the Alberta Department of Agriculture. Furthermore, only small numbers of males were attracted by the unmated females in early tests (Table II). Even though the population was sparse, single attractant traps that were baited with Z7-16:Ac, Z11-16:Ac, and E11-16:Ac in ratios of 2:8:1 and 2:16:1 captured 2.3 and 3.8 males/trap/day from 8 September to 8 October. Similarly, single traps that were baited with the same three components in a ratio of 1:10:1, captured 3.0 and 3.2 males/trap/day from 16 August to 8 September, and of 152 specimens taken, only one was not darksided cutworm (see Table V). Darksided cutworm male moths were also captured in Manitoba in some of the later tests (see Table VI). Two single traps baited with Z7-16:Ac and Z11-16:Ac, and these two components with E11-16:Ac in ratios of 1:10 and 1:10:1, captured an average of 4.5 and 3.8 males/trap/day from 5 August to 27 September. The maxima were 32 and 21 males/trap/day. The attractants were again substantially species specific as only three specimens of the 444 captured were of other species.

Table V

Darksided cutworm male moths captured in single traps baited with 200 mg of a mixture of Z7-16:Ac Z11-16:Ac, and E11-16:Ac in a ratio o 1:10:1 from August 15 to September 8, 1976, in two locations in Alberta

| Trap/date | Trap locations ✦ | | | |
|---|---|---|---|---|
| | A | B* | C | D** |
| 16 August*** | 2 | 0 | 4 | 3 |

Table V-continued

Darksided cutworm male moths captured in single traps baited with 200 mg of a mixture of Z7-16:Ac Z11-16:Ac, and E11-16:Ac in a ratio o 1:10:1 from August 15 to September 8, 1976, in two locations in Alberta

| Trap/date | Trap locations ✦ | | | |
|---|---|---|---|---|
| | A | B* | C | D** |
| 18 | 1 | 0 | 9 | 0 |
| 19 | 3 | 2 | 9 | 1 |
| 22 | 10 | 5 | 13 | 6 |
| 24 | 5 | 4 | 8 | 11 |
| 27 | 5 | 3 | 11 | 4 |
| 29 | 12 | 4 | 9 | 5 |
| 3 September | 16 | 18 | 10 | 14 |
| 8 | 18 | 11 | 6 | 11 |
| Total males | 72 | 47 | 79 | 55 |
| Average males/trap/day | 3.0 | 2.0 | 3.2 | 2.3 |
| Total stray specimens | 0 | 0 | 1 | 1 |

✦ A single trap at Grassy Lake, Alberta, for one night, August 13, 1976, caught 10 males.
*This trap was baited with 1 mg of attractant. Traps A and B were about 30 m apart.
**This trap was baited with 200 mg of the three compounds in a ratio of 2:40:1; traps C and D were about 30 m apart.
***Traps were placed in the field August 15.

Table VI

Traps installed 5 August 1976 in fallow field plots - Attractant formulations "A" and "B"

| | Numbers Captured | | |
|---|---|---|---|
| | Darksided | | |
| Date | "A"* | "B"** | Others |
| 9 Aug. | 2 | 4 | |
| 12 Aug. | 9 | 13 | |
| 13 Aug. | 5 | 6 | |
| 16 Aug. | 15 | 7 | |
| 17 Aug. | 10 | 6 | |
| 20 Aug. | 17 | 12 | |
| 23 Aug. | 32 | 24 | 1 unknown moth in "B" |
| 26 Aug. | 29 | 18 | |
| 27 Aug. | 19 | 15 | |
| 30 Aug. | 15 | 22 | |
| 2 Sept. | 13 | 16 | |
| 3 Sept. | 32 | 21 | 2 unknown moths in "A" |
| 8 Sept. | 30 | 30 | |
| 10 Sept. | 2 | 3 | |
| 27 Sept. | 6 | 8 | |
| Total males captured | 236 | 205 | |
| Average males/trap/day | 4.5 | 3.8 | |

*Formulation A Z7-16:Ac/Z11-16:Ac/E11-16:Ac in ratio 1:10:1 200 μg total
**Formulation B Z7-16:Ac/Z11-16:Ac in ratio 1:10 200 μg total These repeated test results clearly demonstrate the field attractancy and species specificity of the attractant mixture described herein for this darksided cutworm moth. This attractant mixture would be useful for studying, monitoring and helping to control this species.

We claim:

1. An attractant mixture for male moths of the darksided cutworm *Euxoa messoria* (Harris) comprising
    (1) Z-11-hexadecen-1-yl acetate, and
    (2) Z-7 compound selected from Z-7-hexadecen-1-yl acetate and Z-7, Z-11-hexadecadien-1-yl acetate and mixtures thereof,
in ratios of (1)/(2) within about 4:1 to about 40:1, and
    (3) 0 to about 20% by wt. of the total mixture of at least one of the E-isomers E-11-hexadecen-1-yl acetate and E-7-hexadecen-1-yl acetate.

2. The attractant mixture of claim 1 wherein component (2) is Z-7-hexadecen-1-yl acetate.

3. The attractant mixture of claim 1 wherein both of the E-isomers, E-11-hexadecen-1-yl acetate and E-7-hexadecen-1-yl acetate, are present.

4. The attractant mixture of claim 2 wherein the proportion of (1) to (2) is approximately 20:1.

5. The attractant mixture of claim 1 with a liquid or solid carrier.

6. The attractant of claim 5 wherein the carrier is rubber.

7. A method of attracting male moths of the darksided cutworm *Euxoa messoria* (Harris) comprising exposing the moths to the attractant mixture of claim 1 in amounts from about 100 to about 1000 micrograms of said attractant.

* * * * *